(12) United States Patent
Glaug et al.

(10) Patent No.: US 6,544,244 B1
(45) Date of Patent: Apr. 8, 2003

(54) DISPOSABLE ABSORBENT ARTICLE HAVING A REINFORCED FASTENING TAPE LANDING ZONE

(75) Inventors: Frank S. Glaug, Chester Springs, PA (US); Andrew Waksmundzki, Jackson, NJ (US)

(73) Assignee: Tyco Healthcare Retail Services AG, Schaffhausen (CH)

( * ) Notice: Subject to any disclaimer, the term of this patent is extended or adjusted under 35 U.S.C. 154(b) by 0 days.

(21) Appl. No.: 09/522,235

(22) Filed: Mar. 9, 2000

(51) Int. Cl.[7] ............................................... A61F 13/15
(52) U.S. Cl. ..................................................... 604/389
(58) Field of Search ........................ 604/385.24–385.3, 604/386, 389, 390, 393–394, 387

(56) References Cited

U.S. PATENT DOCUMENTS

| | | |
|---|---|---|
| 4,710,190 A | 12/1987 | Wood et al. |
| 4,753,649 A | 6/1988 | Pazdernik |
| 4,764,234 A | 8/1988 | Smits et al. |
| 4,764,242 A | 8/1988 | Gressick et al. |
| 4,911,702 A | 3/1990 | O'Leary et al. |
| 5,024,672 A | 6/1991 | Widlund |
| 5,026,446 A | 6/1991 | Johnston et al. |
| 5,061,262 A | 10/1991 | Chen et al. |
| 5,071,415 A | 12/1991 | Takemoto |
| 5,098,423 A * | 3/1992 | Pieniak et al. ............ 604/385.1 |
| 5,106,383 A | 4/1992 | Mulder et al. |
| 5,236,429 A | 8/1993 | Widlund |
| 5,264,264 A * | 11/1993 | Shibata et al. ................. 428/40 |
| 5,275,588 A | 1/1994 | Matsumoto et al. |
| 5,370,639 A | 12/1994 | Widlund |
| 5,527,305 A | 6/1996 | Goulait et al. |
| 5,599,620 A | 2/1997 | Huskey |
| 5,613,959 A * | 3/1997 | Roessler et al. ............. 604/364 |
| 5,649,921 A | 7/1997 | Arakawa et al. |
| 5,690,628 A | 11/1997 | Huskey et al. |
| 5,720,739 A | 2/1998 | Hilston et al. |
| 5,722,969 A | 3/1998 | Ito et al. |
| 6,086,571 A * | 7/2000 | Guevara et al. ......... 604/385.2 |
| 6,371,951 B1 * | 4/2002 | Koczab et al. ......... 604/385.24 |

* cited by examiner

Primary Examiner—Weilun Lo
Assistant Examiner—C. Lynne Anderson
(74) Attorney, Agent, or Firm—Howson and Howson

(57) ABSTRACT

A disposable absorbent brief is provided with a reinforced fastening tape landing zone which permits repeated removal and reattachment of the fastening tape for adjustment of fit. The backing sheet of the brief is a relatively thin and inexpensive sheet material which has at least one relatively thin and inexpensive, adhesively-secured strip of landing zone reinforcement sheet material. The reinforcement strip provides the strength required to allow tape removal and reattachment without causing tearing of the reinforcement strip or backing sheet or separation of the reinforcement sheet from the backing sheet. The adhesive layer is applied to the reinforcement sheet stock by slot coating as a continuous and uninterrupted layer on the reinforcement strip in a cost-effective and efficient process.

8 Claims, 2 Drawing Sheets

DISPOSABLE ABSORBENT ARTICLE HAVING A REINFORCED FASTENING TAPE LANDING ZONE

FIELD OF THE INVENTION

This invention relates to disposable absorbent articles and more particularly to improvements in adult incontinence briefs of the kind utilizing fastening tapes with pressure-sensitive adhesive for securing parts of the brief together in order to fit the diaper to the person.

BACKGROUND OF THE INVENTION

Disposable absorbent articles, such as infant diapers and adult incontinence products, are used to absorb body fluids and waste materials of infants, children and adults. These products are provided, for example, as briefs or undergarments, and have a moisture absorbent pad covered on one side by a moisture-permeable, body-contacting cover sheet and on the other side by a moisture-impermeable or hydrophobic backing sheet. Typically, the disposable absorbent article is fitted to the wearer by two or more fastening tapes, which are permanently connected to, and extend from, the outside surface of the backing sheet and are adhesively secured to areas of the outside surface of the backing sheet known variously as "target zones" or "landing zones."

After the disposable absorbent article is initially secured on the wearer, adjustment is often necessary in order to obtain a proper fit. Thus, after the fastening tapes are initially secured to the landing zone, detachment and reattachment of the tapes are required in order to carry out the desired adjustment. A backing sheet which is too thin or weak will rip or become damaged when the fastening tape is removed. Thus, to achieve the necessary strength to permit tape removal and reattachment, the backing sheets of disposable absorbent articles are generally made relatively thick. For example, a backing sheet made from a polyethylene film having a uniform thickness of 1.1 mils (0.0011 inch or 0.028 mm) has been found to provide the required strength, even at the low end of the film thickness range, to permit tape removal and reattachment without causing excessive damage to the backing sheet. However, the thickness of the backing material is important only in order to avoid tearing the backing material when the tape is removed from it. The use of thick backing sheet material results in significant material costs, and thus, the backing sheet is not a "value-adding" feature.

As an alternative to relatively thick and expensive backing sheet materials, backing sheets have been provided with reinforced landing zone areas to permit removal and reattachment of the fastening tapes without ripping or otherwise damaging the backing sheet. For example, U.S. Pat. No. 4,911,702 to O'Leary et al. discloses a disposable absorbent adult brief having a backing film with two "target tapes" on a backing having a thickness in the range of 1.0 to 1.3 mil. FIG. 2 of the O'Leary patent illustrates a prior art adult brief having four attachment tabs and two target tapes, the stated purpose of which is to serve as attachment points for the attachment tabs so that, if desired, they may be repositioned without tearing the thin polyethylene backing film.

U.S. Pat. Nos. 5,370,639, 5,024,672 and 5,236,429, to Widlund, disclose a disposable diaper having a polyethylene backing film onto which a plastic strip is glued, and to which pressure-adhesive tapes are secured.

U.S. Pat. No. 5,026,446 to Johnston et al. discloses a method of manufacturing a disposable diaper having a target strip. The target strips are made of high-strength thermoplastic films such as biaxially oriented polypropylene film or biaxially oriented poly (ethylene terephthalate) film having a thickness of 0.6 to 1.6 mil. A roll of pressure-sensitive adhesive tape is first fed through a metal roll and a counter rotating abrasive brush and is then fed onto a vacuum wheel where it is cut into strips by a rotary cutter. Each strip is adhered to a diaper web with pressure applied by a rubber pad on a steel roll.

U.S. Pat. No. 4,710,190 to Wood et al. discloses a disposable diaper having a reinforcement strip made of polypropylene or poly (ethylene terephthalate) film having a thickness of 0.4 to 3.0 mil. A bonding layer secures the strip to the backing film when the strip and backing film are applied with pressure and heat, such as, by a heating roll.

U.S. Pat. Nos. 4,753,649 to Pazdernik; 5,106,383 to Mulder et al., U.S. Pat. No. 5,720,739 to Hilston et al., U.S. Pat. No. 5,649,921 to Arakawa et al. and U.S. Pat. No. 5,599,620 to Huskey disclose various other disposable diapers having reinforcement strips adhesively secured to backing films. U.S. Pat. No. 5,690,628 to Huskey et al., U.S. Pat. No. 5,527,305 to Goulait et al.; 5,061,262 to Chen et al., U.S. Pat. No. 5,275,588 to Matsumoto et al. and U.S. Pat. No. 5,722,969 to Ito et al. disclose various other disposable diapers having reinforced landing zones.

Although the aforementioned disposable absorbent articles having reinforced landing zones, and their methods of manufacture, may be satisfactory for their intended purposes, there remains a need for an improved disposable absorbent article which permits tape removal and re-fastening and which can be produced at lower cost. There is also a need for an improved, more efficient and cost-effective method of producing a disposable absorbent article having a reinforced landing zone.

BRIEF SUMMARY OF THE INVENTION

The principal object of this invention is to provide a disposable absorbent article, adapted to be worn on the person, which has a reinforced landing zone permitting tape removal and re-fastening, and which can be produced at a very low cost. An additional object of this invention is to provide an efficient and cost-effective method of producing a disposable absorbent article having a reinforced landing zone.

The invention addresses the foregoing objects in a disposable absorbent article comprising a thin, liquid-impermeable backing sheet having a uniform thickness, preferably in the range of 0.3 to 0.9 mil, and opposite inner and outer faces. An absorbent layer is secured to the inner face, and tapes, secured to first and second areas on the outer face of the backing sheet have portions extending therefrom coated by a pressure-sensitive adhesive. The pressure-sensitive adhesive is sufficiently aggressive and the backing sheet is sufficiently thin, that if the tapes were adhered by the adhesive directly to the outer face of the backing sheet, they could not be removed consistently from the backing sheet without ripping the backing sheet. Reinforcement sheets, which are preferably of uniform thickness in the range of about 0.2 to 0.9 mil, are secured to the outer face of the backing sheet to establish landing zones for attachment of the adhesive-coated portions of the tapes. These reinforcement sheets are secured to the outer face of the backing sheet respectively over third and fourth, preferably rectangular, areas. The reinforcement sheets are secured respectively to the third and fourth areas of the outer face of the backing sheet by layers of adhesive which are uninterrupted widthwise and lengthwise over each of the third and fourth areas.

A key to the achievement of highly superior results with the invention is the application of the layer or layers of adhesive to the reinforcement sheets by slot coating. Slot coating produces the uninterrupted area coverage, and thereby prevents gaps in the adhesive layer which could result in ripping of the reinforcement sheets or separation of the reinforcement sheets from the backing sheet. It also enhances efficiency in adhesive usage, produces a uniform adhesive coating thickness, and provides well-defined margins along opposite edges of the reinforcement strips, thereby avoiding areas of exposed adhesive which could result in portions of the article adhering to one another or to other, similar articles.

Another key to the achievement of highly superior results with the invention is the application of hot melt adhesive to a thin, heat-sensitive polymeric film. One method to achieve this is first to "slot coat" the hot melt adhesive to a low friction, smooth roll (made of PTFE, or having a silicone or PTFE coating), which is cooled as well. Rolls of this kind are known as "chill rolls." The chill roll is then rotated to transfer coat the lower temperature hot-melt adhesive to a polymeric film. The hot melt adhesive, which is a pressure-sensitive adhesive, sticks to the higher friction polymeric film and is thus transferred completely from the chill roll to the film.

Other objects, details and advantages of the invention will be apparent from the following detailed description when read in conjunction with the drawings.

DETAILED DESCRIPTION

The invention will be described with reference to an adult incontinence brief, in which the advantages of the invention are most conspicuous. However, it will be apparent from the description which follows, that advantages of the invention can be realized in other absorbent articles, including infant diapers.

The disposable absorbent article 10 has a construction which permits the article to be adjusted to ensure a proper and comfortable fit. To this end, the article 10 has a reinforced backing sheet 12 which permits removal and reattachment of tape fasteners 14 so that, after the article is initially positioned on the wearer, it can be readily adjusted for a proper and comfortable fit.

Typically, material and manufacturing costs are relatively high for a disposable absorbent article having an extra-strength, or reinforced, backing sheet. A significant aspect of this invention is that the absorbent article 10 is inexpensive to produce even though it utilizes a reinforced backing sheet. Material costs are minimized by a unique construction and manufacturing costs are minimized by a novel and cost-effective method of manufacture. The construction and manufacturing technique can be utilized for both infant diapers and adult briefs, but are particularly advantageous in the manufacture of adult briefs because of the requirements for larger sizes of sheet material and a greater number of relatively strong fastening tapes.

Figure 1:
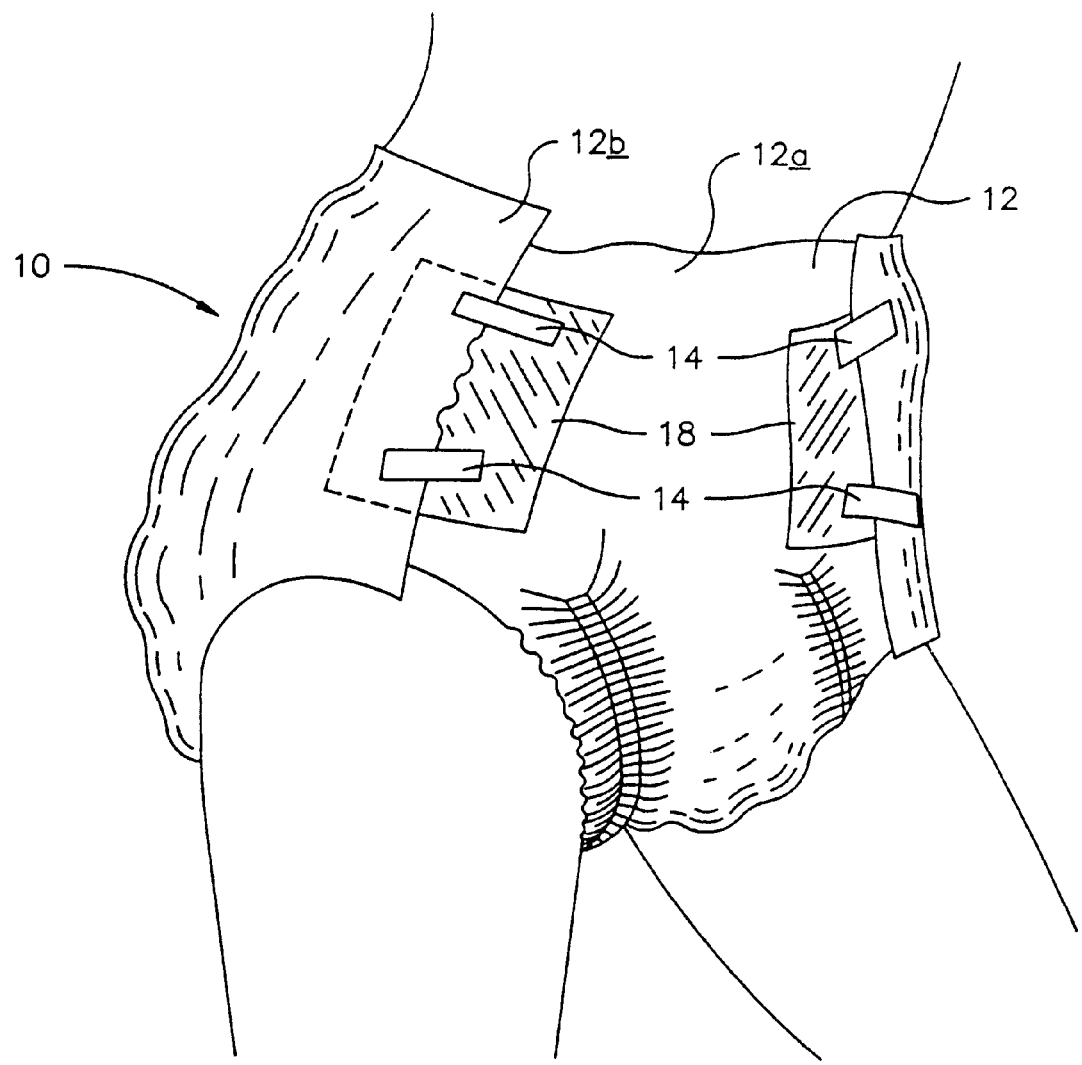
FIG. 1 is a perspective view of a disposable absorbent brief secured on a wearer according to the invention.
Figure 2:
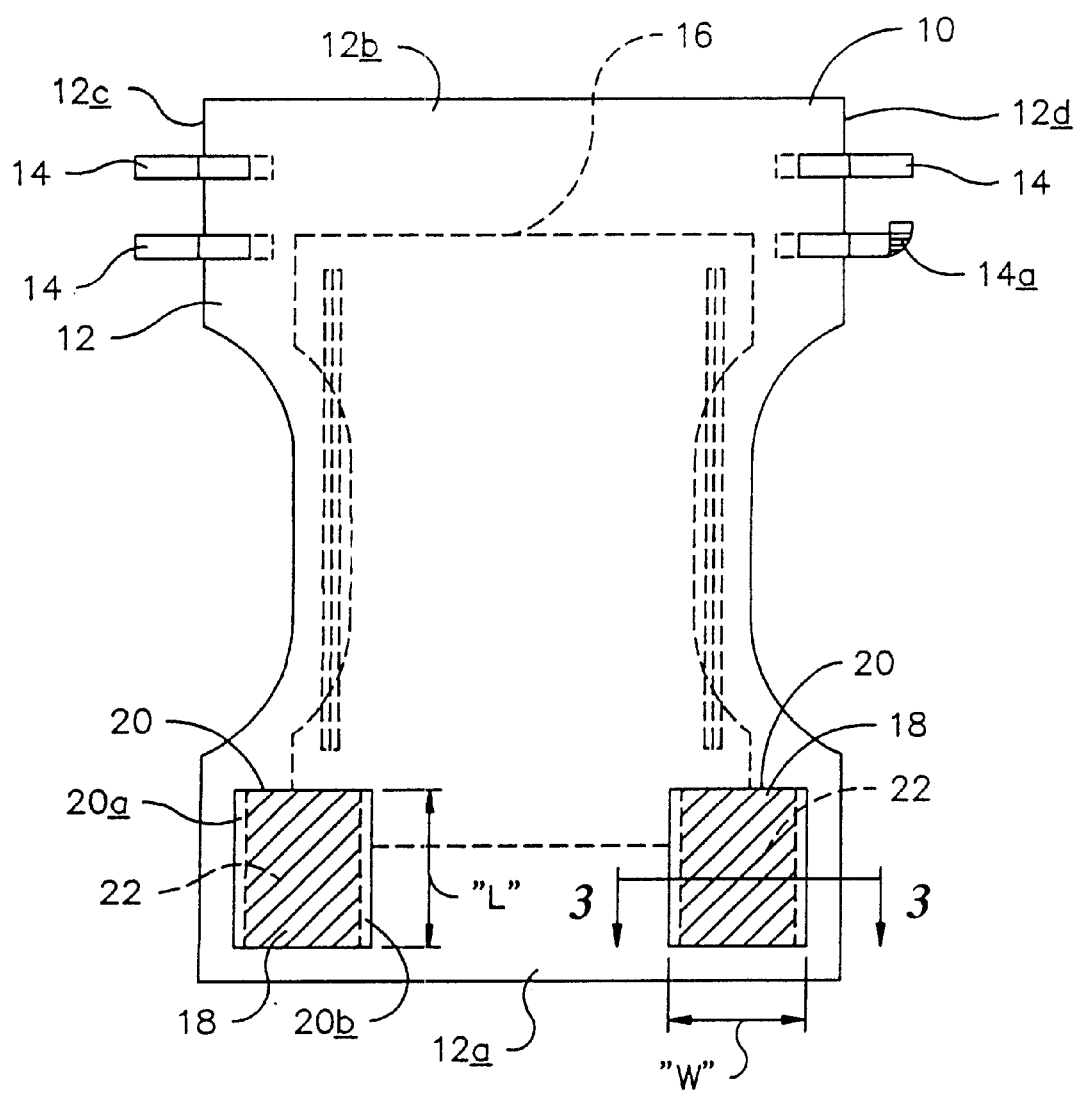
FIG. 2 is a plan view of the disposable absorbent brief of FIG. 1 disposed in a flat condition.

In FIG. 2, the outer face of the backing sheet 12 is seen in full, and the moisture absorbent pad 16 is shown in broken lines on the opposite, inner face of the backing sheet. The pad is secured to the inner face of the backing sheet, and covered by a moisture-permeable, body-contacting cover sheet (not shown) which may be coextensive with the backing sheet, or alternatively large enough to cover the absorbent pad but smaller than the backing sheet so that the backing sheet has a margin extending beyond the edges of the moisture-permeable cover sheet. As best illustrated in FIG. 1, the backing sheet 12 has an abdominal portion 12a and a rear portion 12b, and as best illustrated in FIG. 2, the rear portion of the backing sheet has opposite side edges 12c and 12d.

Plural fastening tapes 14 extend laterally from the rear portion 12b of the backing sheet, beyond the edges 12c and 12d so that, when the brief 10 is positioned on the wearer, the fastening tapes 14 extend forward and can be attached to the abdominal portion 12a of the backing sheet. Preferably, an adult brief 10, as illustrated, will include a pair of fastening tapes 14 extending from each backing sheet side edge, 12c and 12d. A pressure-sensitive adhesive on the inward facing sides 14a of the fastening tapes 14 have permits the tapes to be secured to the backing sheet to attach the brief 10 to the wearer, and permits subsequent removal and reattachment.

Figure 3:
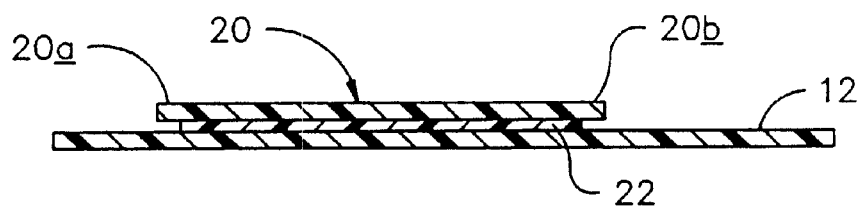
FIG. 3 is a cross-sectional view of the disposable absorbent brief taken on plane 3—3 of FIG. 2.

The backing sheet 12 has two reinforced landing zones 18 to which the fastening tapes 14 may be attached. Each landing zone 18 is provided by a separate strip of material 20 permanently secured, by a layer 22 of adhesive, to the abdominal portion 12a of the outer face of the backing sheet. The layer of adhesive is also illustrated in FIG. 3, and its area of coverage is illustrated by dotted lines in FIG. 2. Reinforcement strip 20 must be secured to the backing sheet 12 in such a way as to avoid ripping of the strip 20 or the backing sheet 12, and also to avoid separation of the strip 20 from the backing sheet 12, when the fastening tapes 14 are pulled away from the landing zone 18 for adjustment. For example, if the adhesive layer 22 is not continuous, air pockets between the reinforcement strip 20 and backing sheet 12 will allow the reinforcement strip 20 to tear and/or separate from the backing sheet 12. Therefore, an important aspect of the invention is that the adhesive layers 22 are uninterrupted widthwise and lengthwise over the areas which they cover. Thus, if the layer of adhesive is rectangular, which is the preferred configuration for manufacturing efficiency, the adhesive layer covers the entire area within the borders of the rectangle. More generally, for a rectangular adhesive layer, or any other suitable shape, the adhesive layer is uninterrupted lengthwise and widthwise if substantially any straight path lying in the plane of the layer of adhesive and intersecting an edge of the adhesive layer, passes through adhesive substantially continuously and without interruption by a gap in the adhesive layer until it finally exits from the adhesive layer through an edge on the other side of the adhesive layer. Thus, the border of any adhesive layer will generally be either straight or convex at all locations. However, minor concavities are not objectionable.

Preferably, the continuous and uninterrupted layer of adhesive 22 is applied to the reinforcement strips 20 by a slot-coating process. In this process, the adhesive layer 22 extends the full length "L" of the reinforcement strip 20, but slightly less than the full width "W" of the reinforcement strip 20 as best illustrated in FIG. 2 by dotted lines. Thus, a pair of side edge margins, 20a and 20b, of the reinforcement strip 20 freely extend from the backing sheet 12 along opposite edges of the adhesive layer 22. The margins, 20a and 20b, do not form a part of the landing zone area 18 and are located so that the tape fasteners 14 are never secured to them. The application of adhesive to the strip material by slot coating results in several advantages. First, slot coating produces a continuous adhesive layer without gaps or air pockets which would allow ripping or separation to take place upon removal of the attachment tapes. Second, slot coating permits application of the adhesive in such a way as to provide the narrow margins 20a and 20b in the reinforcement strips along opposite edges of the adhesive area. These narrow margins avoid exposed adhesive that could cause parts of the article 10 to adhere to one another or cause adjacent articles 10 to adhere to each other in manufacture, or in the process of packaging the articles. Third, slot coating improves the efficiency of adhesive usage by avoiding application of adhesive to coating machine parts and to areas where it is not needed, and by producing a uniform adhesive coating having an optimum thickness.

Another important aspect of the invention is that the use of a continuous and uninterrupted layer of adhesive 22 permits the use of relatively thin and inexpensive sheet materials for the backing sheet 12 and reinforcement strips 20. For example, the sheet material for either the backing sheet or the reinforcement strips can be polyethylene, polypropylene, a co-polymer blend, co-extruded film, polyester or polyurethane. The backing sheet and reinforcement strips can be made of the same sheet material or of different sheet materials. Preferably, the backing sheet 12 has a uniform thickness of about 0.3 to 0.9 mils, and each reinforcement strip 20 has a uniform thickness of about 0.2 to 0.9 mils.

By way of example, one contemplated embodiment of article 10 utilizes a backing sheet 12 made of polyethylene having a thickness of 0.8 mils and reinforcement strips 20 made of polypropylene having a thickness of 0.5 mils. In this embodiment, the combined thickness of the polyethylene and polypropylene components of each landing zone area 18 is 1.3 mils, and the thickness of the remaining portions of the backing sheet is 0.8 mils. Thus, the material usage in the construction of the backing sheet is optimized by reinforcing only the area to which the tape fasteners 14 are likely to be attached in normal use. In addition, the use of a continuous and uninterrupted layer of adhesive 22 permits further reduction in the thickness of the reinforcement strip material. The embodiment is thereby produced inexpensively, but permits repeated removal and reattachment of the attachment tapes In the manufacture of the disposable absorbent article 10, a continuous, elongate, advancing strip of landing zone reinforcement material is transfer coated with a pressure sensitive adhesive. Preferably, a slot-coating process is utilized, in which an adhesive is extruded through an elongate narrow slot onto a PTFE chill roll or a PTFE- or silicone-coated chill roll, and than transferred to the advancing reinforcement material. To this end, the slot extends transversely relative to the advancing elongate strip of material so that the reinforcement material is transfer coated with a continuous elongated layer of adhesive 22. The width of the slot is slightly less than the width of the reinforcement material so that the opposite side edge margins 20a and 20b of the reinforcement material are not covered by the adhesive layer. Slot-coating ensures that the layer of adhesive 22 is continuous and uninterrupted, and provides for cost-effective and efficient coating of the reinforcement material and avoidance of exposed adhesive.

Preferably, the adhesive is a low-temperature processing, pressure sensitive, construction adhesive. An example of such an adhesive is an adhesive sold under the trademark COOL-LOK by National Starch & Chemical of Bridgewater, N.J.

In the slot-coating process, when the temperature sensitive adhesive is transferred from the elongate narrow slot to the chill roll, the temperature of the adhesive is in the range of about 150° to 350° F. (66° to 177° C.), preferably at approximately 200° F. (93° C.). The temperature of the adhesive is at a lower level when it is transferred from the chill roll onto the elongated strip of landing zone material.

After the elongate strip of landing zone reinforcement material is coated with adhesive, the material is transferred onto a vacuum roll and then cut on a rotary die to produce multiple, individual landing zone reinforcement strips 20. The individual landing zone reinforcement strips 20 are applied directly onto the outer faces of backing sheets 12.

The above-described disposable absorbent article and method of manufacture of the article provide a brief having a reinforced backing sheet which permits repeated removal and reattachment of fastening tapes. Material costs and manufacturing costs are minimized by utilizing thin and inexpensive sheet materials and a applying a continuous and uninterrupted layer of pressure sensitive adhesive onto the reinforcement strips by slot-coating.

While a preferred disposable absorbent article and method of its manufacture have been described, various modifications can be made to the brief construction and to the method of manufacture. For example, the number of tapes for attachment to each landing zone can be varied from one in the case of an infant diaper, to two or more in the case of an adult brief. Although the illustrated embodiment has a pair of landing zones 18 in order to minimize the amount of material needed for strips 20, one elongate landing zone, extending across the abdominal portion 12a of the backing sheet 12, could be utilized instead. The thicknesses of the backing sheet and reinforcing strips are desirably kept at a minimum, but can be varied. Moreover, the thicknesses of the backing sheet and reinforcing strips can be identical or different from each other. The reinforcing strips, although preferably rectangular for convenience of manufacture, can be provided in other shapes, such as circular or oval, provided that the adhesive layer has no gaps permitting ripping of the reinforcement strips or detachment of the reinforcement strips from the backing layer. Other modifications, alterations, and changes may be made without departing from the spirit and scope of the invention as defined in the appended claims.

We claim:

1. A disposable absorbent article adapted to be worn on the person, comprising a moisture absorbing pad situated between a moisture-permeable cover sheet and a moisture-impermeable or hydrophobic backing sheet, and at least a pair of fastening tapes extending from said backing sheet for securing portions of the article together to hold the article to a wearer's body; said backing sheet being made of a material having a thickness in a range of about 0.3–0.9 mil and having a reinforced landing zone permitting removal and reattachment of said fastening tapes to and from said backing sheet, and said landing zone being provided by an additional piece of sheet material which has a thickness in a range of about 0.2–0.9 mil and which is secured to said backing sheet by a thin and continuous layer of adhesive;

wherein said additional piece of sheet material providing the landing zone has a face which confronts said backing sheet;

wherein said thin and continuous layer of adhesive is slot coated onto said face of said additional piece of sheet material such that said layer of adhesive covers less than the entire surface area of said face;

wherein said landing zone is a substantially rectangular strip of material selected from the group consisting of polypropylene, polyethylene, co-polymer blend, co-extruded film, polyester and polyurethane; and wherein all of said surface area of said face of said additional piece of sheet material is coated with said thin, continuous layer of adhesive except for a pair of opposite peripheral edge margin portions of said rectangular strip.

2. A disposable absorbent article according to claim 1, wherein said backing sheet is made of a material selected from the group consisting of polypropylene, polyethylene, co-polymer blend, co-extruded film, polyester and polyurethane.

3. A disposable absorbent article according to claim 1, wherein said additional piece of sheet material is polypropylene.

4. A disposable absorbent article according to claim 1, wherein said backing sheet material is polyethylene.

5. A disposable absorbent article according to claim 1, wherein said adhesive is a pressure sensitive adhesive.

6. A disposable absorbent article according to claim 1, wherein said backing sheet has a second reinforced landing zone permitting removal and reattachment of fastening tapes to and from said backing sheet, said second landing zone being provided by a second, additional piece of sheet material which has a thickness in a range of about 0.2–0.9 mil and which is secured to said backing sheet by a second, thin and continuous layer of adhesive, wherein said second, additional piece of sheet material has a face which confronts said backing sheet, and wherein said second thin and continuous layer of adhesive is slot coated onto said face of said second, additional piece of sheet material such that said second layer of adhesive covers less than the entire surface area of said face of the second, additional piece of sheet material, and at least two additional fastening tapes extending from said backing sheet and engageable with said second landing zone.

7. A disposable absorbent article having a moisture absorbent pad enclosed within a moisture permeable body contacting cover sheet and a moisture impermeable or hydrophobic backing sheet, said backing sheet comprising a sheet of polyethylene having a thickness in a range of about 0.3–0.9 mil and having a reinforced landing zone for at least one fastening tape extending integrally from said backing, said landing zone being a strip of polypropylene adhesively secured to an outer surface of said backing sheet by a continuous layer of adhesive, and having a thickness in a range of about 0.2–0.9 mil, wherein said continuous layer of adhesive is slot coated onto a face of said landing zone strip and continuously covers all of said face except for a pair of opposed edge margins of said face.

8. A disposable absorbent article according to claim 7, wherein said backing sheet has a second reinforced landing zone extending integrally from said backing, said second landing zone also being a strip of polypropylene adhesively secured to an outer surface of said backing sheet by a second continuous layer of adhesive, and having a thickness in a range of about 0.2–0.9 mil, wherein said second continuous layer of adhesive is slot coated onto a face of said second landing zone strip and continuously covers all of said face of the second landing zone strip except for a pair of opposed edge margins of said face of the second landing zone strip, and the article including at least four fastening tapes extending integrally from said backing, at least two said fastening tapes being engageable with one of said landing zone strips and at least two other fastening tapes being engageable with the other of said landing zone strips.

* * * * *